(12) United States Patent
Von Schuckmann

(10) Patent No.: US 10,722,665 B2
(45) Date of Patent: Jul. 28, 2020

(54) HANDSET FOR DELIVERING A PHARMACEUTICAL SUBSTANCE

(71) Applicant: Alfred Von Schuckmann, Kevelaer (DE)

(72) Inventor: Alfred Von Schuckmann, Kevelaer (DE)

( * ) Notice: Subject to any disclaimer, the term of this patent is extended or adjusted under 35 U.S.C. 154(b) by 429 days.

(21) Appl. No.: 15/532,360

(22) PCT Filed: Dec. 4, 2015

(86) PCT No.: PCT/EP2015/078624
§ 371 (c)(1),
(2) Date: Jun. 1, 2017

(87) PCT Pub. No.: WO2016/091737
PCT Pub. Date: Jun. 16, 2016

(65) Prior Publication Data
US 2018/0015239 A1    Jan. 18, 2018

(30) Foreign Application Priority Data

Dec. 9, 2014   (DE) .......................... 10 2014 118 248

(51) Int. Cl.
*A61M 15/00*    (2006.01)
(52) U.S. Cl.
CPC ........ *A61M 15/0025* (2014.02); *A61M 15/00* (2013.01); *A61M 15/009* (2013.01); *A61M 15/0023* (2014.02); *A61M 15/0026* (2014.02)
(58) Field of Classification Search
CPC ........ A61M 15/00–08; A61M 15/0023; A61M 15/0025; A61M 15/0026
See application file for complete search history.

(56) References Cited

U.S. PATENT DOCUMENTS

| 2,620,061 | A | 12/1952 | Uxa |
| 5,896,853 | A | 4/1999 | Howlett |
| 5,899,200 | A | 5/1999 | McNary |
| 7,073,679 | B1 | 7/2006 | Lagler et al. |
| 8,387,615 | B2 | 3/2013 | Bunce |

(Continued)

FOREIGN PATENT DOCUMENTS

| DE | 697 23 156 T2 | 5/2004 |
| EP | 1 147 054 A1 | 10/2001 |

(Continued)

OTHER PUBLICATIONS

International Search Report of PCT/EP2015/078624, dated Feb. 18, 2016.

*Primary Examiner* — Bradley H Philips
*Assistant Examiner* — Matthew Standard
(74) *Attorney, Agent, or Firm* — Collard & Roe, P.C.

(57) ABSTRACT

The invention relates to a handset (1) for delivering a pharmaceutical substance, with a housing (2) that exhibits a mouthpiece (8), wherein the mouthpiece (8) can be sealed with a cap (9), and the cap (9) is attached to the housing (2) by means of a spring (16), and can be swiveled around a swivel axis (x) to release the mouthpiece (8). In order to further improve a handset of the kind in question, in particular as relates to attaching the cap to the handset, it is proposed that the spring (16) have an angled progression in a top view, in which the swivel axis (x) is imaged as a line.

4 Claims, 5 Drawing Sheets

(56) References Cited

U.S. PATENT DOCUMENTS

| | | | |
|---|---|---|---|
| 8,397,714 B2* | 3/2013 | Pearson | A61M 15/009 128/200.14 |
| 2008/0035681 A1 | 2/2008 | Skillin | |
| 2010/0065589 A1 | 3/2010 | Skillin | |
| 2013/0213394 A1 | 8/2013 | Anderson et al. | |

FOREIGN PATENT DOCUMENTS

| | | |
|---|---|---|
| EP | 1 696 987 A1 | 9/2006 |
| GB | 2 294 506 A | 5/1996 |
| WO | 2005/046774 A1 | 5/2005 |

* cited by examiner

HANDSET FOR DELIVERING A PHARMACEUTICAL SUBSTANCE

CROSS REFERENCE TO RELATED APPLICATIONS

This application is the National Stage of PCT/EP2015/078624 filed on Dec. 4, 2015, which claims priority under 35 U.S.C. § 119 of German Application No. 10 2014 118 248.0 filed on Dec. 9, 2014, the disclosures of which are incorporated by reference. The international application under PCT article 21 (2) was not published in English.

The invention initially relates to a handset for delivering a pharmaceutical substance, with a housing that exhibits a mouthpiece, wherein the mouthpiece can be sealed with a cap, and the cap is attached to the housing by means of a spring, and can be swiveled around a swivel axis to release the mouthpiece.

Handsets of the kind in question are known. For example, the latter are used for inhaling pharmaceutical substances, for e.g., for inhaling powdery preparations or for inhaling aerosols containing pharmaceutical substances.

For example, the handset accommodates a container for the aerosol or forms a receptacle of a carrier, for example a blister or capsule for powder inhalation. The handset has a mouthpiece, which is enveloped by the lips of the user for inhaling the substance.

Also known in this regard is to seal the mouthpiece with a cap when not using the handset. In this conjunction, there exists the necessity to attach the cap to the handset secured against loss. Various solutions are known in this regard. For example, a spring attachment and release of the mouthpiece by swiveling the cap around a swivel axis are known from DE 697 23 156 T2 (U.S. Pat. No. 5,896,853 A). The spring consists of a film hinge like joint. Known from U.S. Pat. No. 2,620,061 A is a cap on a housing that can rotate around a joint axis, wherein the cap is exposed to a helical spring through which the axis extends. Known from GB A 2 294 506 is a handset with a mouthpiece and a cap that seals the latter, in which the cap is attached to the housing by means of a band element, which is in an inwardly crimped section in the sealed state of the cap. In a top view, in which the swivel axis of the band element is imaged as a line, the latter has a straight progression. Known from WO 2005/046774 A1 is a handset with a mouthpiece and a cap that seals the latter, wherein the cap is attached to a band element connected with the housing shiftably, but secured against loss.

With respect to prior art, reference is further to be made to EP 1 696 987 A1, US 2013/213394 A1, EP 1 147 054 A1, US 2010/065589 A1 and US 2008/035681 A1.

Proceeding from the initially mentioned prior art, the object of the invention is to indicate an advantageous configuration of a handset with a cap that seals a mouthpiece.

This object is achieved in the subject matter of claim 1, with the objective being that the cap can be displaced against a prestress of the springs in the opening direction, that the spring exhibits two spring arms, which are joined with the cap at two fastening points spaced apart transversely in the opening direction, that the spring arms are brought together on the casing side in a shared attachment region, which is swivelably connected with the housing by a hinge, and that the cap together with the attachment region can be downwardly swiveled under a housing floor.

The angled progression arises in at least one spring position. The angled progression preferably arises at least in the released spring position, and also in a spring clamping position of the usual kind for removing the cap from the mouthpiece. The angled progression can also be present in any spring position between the released position and the maximally tensioned position for conventional use.

In terms of the top view, the progression of the spring has at least one section that includes an angle of less than 180° relative to another adjoining spring section.

The angled progression permits an improved spring effect. In addition, this makes it possible to lengthen the effective spring path.

The spring has two spring arms, which are connected with the cap at two fastening points spaced apart transversely to the opening direction.

Arranging two spring arms spaced apart from each other in the opening direction makes it possible to achieve a stable, spring-loadable attachment of the cap to the housing.

Both spring arms can have an angled progression in a top view, in which the swivel axis is imaged as a line.

The angled progression of one spring arm can mirror the angled progression of the other spring in relation to the top view.

Because the spring or a spring arm as viewed over the length can run partially counter to the opening direction with one directional component in a released state, the spring or a spring arm is at least partially provided with a section that has a directional component opposite the direction in which the cap is removed from the mouthpiece or a directional component in the direction in which the cap is attached to the mouthpiece. This advantageously provides a length reservoir for the spring or spring arm when tensioning the spring in the process of removing the cap from the mouthpiece.

Given a displacement of the cap in the opening direction, the change in length of the spring or spring arm between the cap and the attachment of the spring to the housing preferably does not or only insignificantly result(s) from a given elasticity of the spring material, but rather from the addition of spring length from a reservoir section of the spring. In an extreme tensioned situation of the cap, this could potentially lead to a point where the spring or spring arm runs in an at least approximately elongated, linear manner between the attachment to the cap and fastening point on the housing or on a section allocated to the housing, utilizing the entire length reservoir.

The spring arms can face away from the attachment to the cap and be brought together on the housing side in a shared attachment region. The attachment region is preferably a rigid section, i.e., one that cannot be spring loaded.

The attachment region can directly be a housing section. The attachment region can also be a section allocatable to the housing, for example such as an integral section of a spring element.

The attachment region is swivelably connected with the housing by a hinge. The respective swivel axis preferably runs transversely directed to the opening direction of the cap. The swivel axis, in particular the geometric swivel axis, can also extend in a plane defined by the spring or spring arms.

The spring arms can further extend in a surface which, in the sealed state, i.e., with the cap placed on the mouthpiece, runs adjusted to an allocation surface of the housing. The extension surface of the spring arms preferably runs parallel to an allocated surface of the housing. The spring arms of the spring can also be supported at least partially on this allocation surface of the housing.

The cap can abut against the housing exposed to a prestress in the sealed position. In the sealed position of the mouthpiece, the spring arms thus are preferably not present in their released state, but rather reserve a stress. This supports the sealed position of the cap.

In order to remove the cap, the latter must be moved against the force of the spring or spring arms in the opening direction.

The attachment region can have an axial formation on the housing side. This axial formation is suitable for swiveling the attachment region, and hence preferably the entire spring with the cap relative to the housing. The attachment region, and thus also the spring with the attached cap, can be plug-assigned. To this end, the housing can have a clip-in formation for the axial formation of the attachment region. The clip-in formation can be designed in such a way that an established clip connection between the housing and attachment region cannot be released, or at least not without a tool.

The spring can have a W-shaped design as viewed from above, wherein a W-central region is (also) provided by the attachment region. The outer W-legs essentially comprise the spring arms. The comparatively considered inner W-legs can be the spring arm sections that run against the opening direction, partially with a directional component. These spring arm sections are preferably secured to the attachment region.

The spring or a spring arm has at least one length that reaches from a fastening point on the housing up to the cap, wherein sections of the spring can indeed also not be spring-loaded (for example, the attachment region). Furthermore, the spring can have a larger extension from one fastening point on the housing to a fastening point on the cap in the closed position than in a released state, but a smaller extension than when removing the cap from the mouthpiece.

Proceeding from the attachment region, a spring arm can be designed in such a way that it can swivel inwardly around a swivel axis running perpendicular to the opening direction or perpendicular to the top view.

The spring or spring arms can also move solely in the plane described by the spring arms, i.e., preferably both during the movement to remove the cap from the mouthpiece and while placing on the cap. Therefore, both in the stressed or released state, the spring or spring arms preferably move in the same plane in which the attachment region further preferably also extends.

A wall section of the cap can also extend in the plane described by the spring and preferably also by the attachment region, preferably a longitudinal wall section of the latter that in particular envelops the spring.

The invention will be explained in more detail below based on the attached drawing, which only shows an exemplary embodiment. Shown on:

Figure 1:
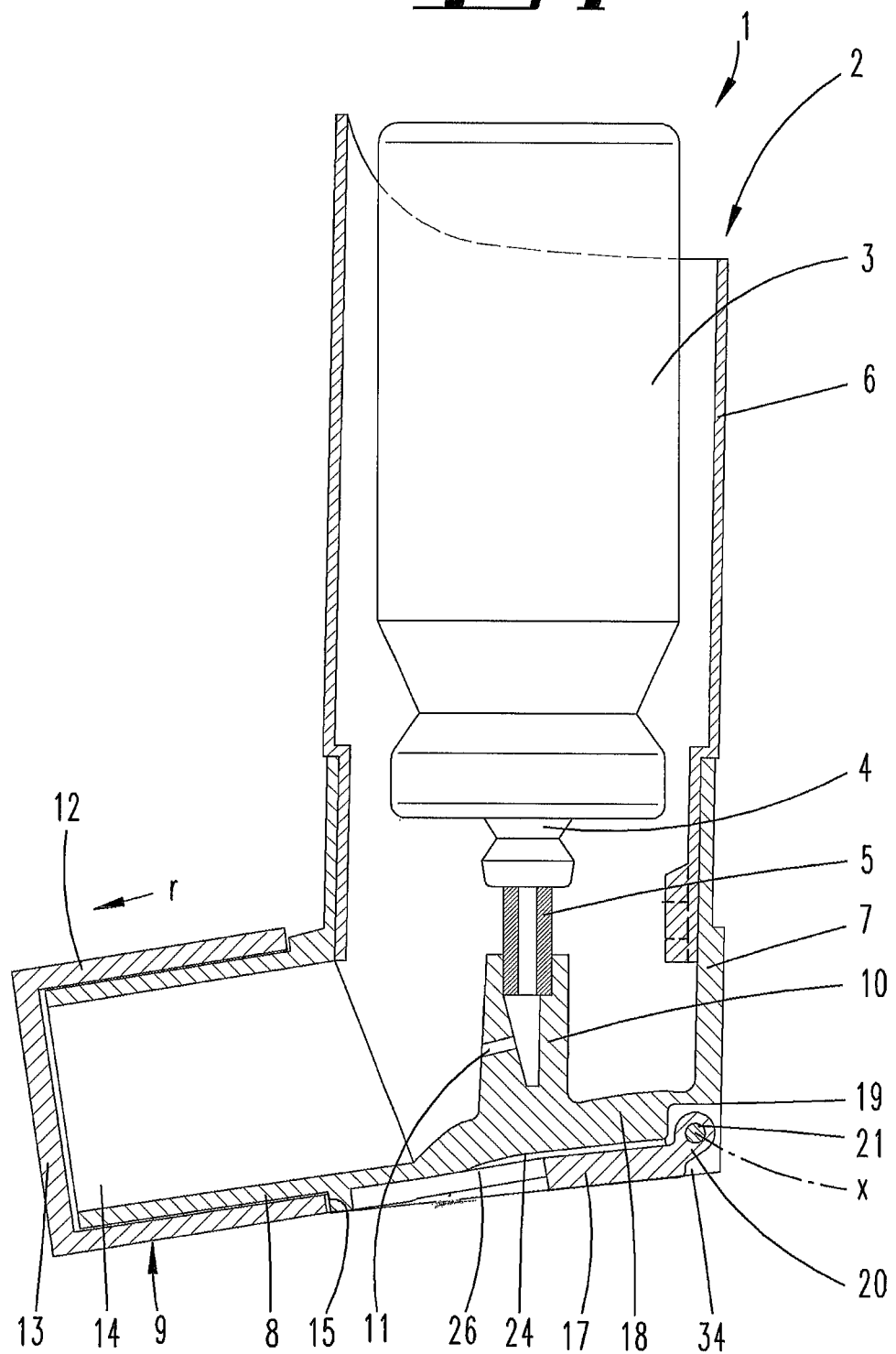
FIG. 1 is a longitudinal section of a handset for delivering a pharmaceutical substance with a mouthpiece sealed by a cap.

A handset for delivering a pharmaceutical substance is illustrated and described, initially with reference to FIG. 1.

The handset 1 has a housing 2, into which a cartridge 3 containing the sprayable substance can be placed. This cartridge 3 can be axially displaced in the housing 2.

In a conventional manner, the cartridge head 4 has a central valve tube 5 extending coaxially to the cartridge 3. The latter is used to deliver medication via an axial relative movement between the cartridge 3 and housing 2.

The housing 2 can be divided into two parts, and essentially consist of two ring parts 6 and 7 arranged one over the other, of which the upper ring part 6 is shaped like a shaft, and the lower ring part 7 has a mouthpiece 8 aligned roughly transverse to the shaft extension. The latter can be sealed by a cap 9.

The valve pipe 5 of the cartridge 3 abuts in an allocated, tubular support section 10 inside of the lower ring part 7, while the cartridge can move axially inside of the shaft-like ring part 6 enveloping the cartridge 3.

The support section 10 that accommodates the valve pipe 5 of the cartridge 3 through clamping and is formed inside of the lower housing ring part 7 is provided with a flow channel 11 having a reduced diameter by comparison to the section that accommodates the valve pipe end, which is fluidically connected with the valve pipe 5, wherein the end of the flow channel 11 facing away from the valve pipe 5 points in the direction toward the mouthpiece 8.

The two ring parts 6 and 7 are plugged together in the exemplary embodiment shown. As an alternative, the two parts can also be interconnected by a thread, for example a coarse thread with a high pitch.

The two-part housing 2 along with the cap 9 are preferably fabricated as plastic injection molded parts.

In the sealed position, the essentially pot-shaped cap 9 bridges over the tubular mouthpiece 8 in such a way that the continuous wall 12 of the cap that comprises the pot wall envelops the mouthpiece 8, and a pot bottom-type cap cover 13 bridges over the mouthpiece opening 14.

The cap 9 inserted onto the mouthpiece 8 acts as a stop limiter by pressing against a preferably continuous stage 15 of the ring part 7 formed on the root side of the mouthpiece 8.

The cap insertion position according to FIG. 1 is preferably secured against latching, for which purpose latching means and counter-latching means are provided on the cap and mouthpiece side (not shown).

The cap 9 is mounted to the housing 2 or ring part 7 secured against loss.

To this end, a spring 16 is attached to the cap 9. It is preferably designed as a single piece and integrally with the cap 9. The spring 16 has an angled progression as viewed from the top, for example see FIG. 5, in which a swivel axis x around which the cap 9 can swivel to release the mouthpiece is imaged as a line. In the view on FIG. 5, i.e., the mentioned top view, the swivel axis in the drawing plane runs like a quasi-endless line, but only one section thereof is graphically depicted.

Facing away from the cap 9, the spring 16 transitions into an attachment region 17 that is likewise preferably designed as a single piece and integrally with the spring 16 and cap 9.

By way of the attachment region 17, the cap 9 as a whole along with the spring 16 and attachment region 17 is fastened to the housing 2, in particular to the ring part, so that it can swivel.

The swivelable fixation is provided on the floor side of the ring part 7, further in particular in a corner transitional region—in relation to a longitudinal sectional view according to FIG. 1—from the housing floor 18 into the continuous wall of the ring part 7.

In this corner region, the ring part 7 is provided with a trough-like depression 19. The latter incorporates an end section 20 of the attachment region 17 that overall is essentially circularly cylindrical.

The resulting geometric swivel axis is transversely directed to a central body axis of the ring part 6 enveloping the cartridge 3.

An axis 21 is provided, and intersected by the swivel axis centrally in the longitudinal direction of the axis 21. The axis 21 [extends] axially over one or both end sections 20, and engages into correspondingly positioned boreholes 22 in the ring part 6.

The attachment region 17 is designed as a plate-like rigid element, with a broad face that runs at least approximately parallel to the allocation surface 24 of the housing floor in the sealed position of the mouthpiece according to FIG. 1, and corresponds to a multiple, for example of seven to fifteen, of the material thickness of the attachment region 17 viewed perpendicular hereto.

Proceeding from the end section 20, the attachment region 17, relative to the sealed position of the mouthpiece depicted on FIG. 1, extends over roughly half the shortest distance arising between the end section 20 and facing peripheral edge of the cap 9.

Furthermore, the attachment region 17 preferably extends at least approximately in a shared surface with the lower side wall section of the cap wall 12.

The spring 16 also preferably and at least extends in this shared surface in the sealed position of the mouthpiece.

The spring 16 has two spring arms 25, 26. These are connected with the cap 9 at one end at two fastening points 27, 28 spaced apart from each other transversely to an opening direction r of the cap 9. The fastening points 27, 28 are preferably formed on the face of the opening edge of the cap 9, in particular on the edge section of the wall bridging under the mouthpiece 8.

The distance between the fastening points 27 and 28 can be adjusted to the inner aperture of the cap 9 viewed in the same direction.

Facing away from the fastening points 27, 28, the spring arms 25 and 27 are fastened to the attachment region 17 in the free end region facing away from the end section 20.

The distance between the fastening points at the attachment region 17 roughly corresponds to one third to half the distance between the fastening points 27, 28 on the cap 9.

Figure 5:
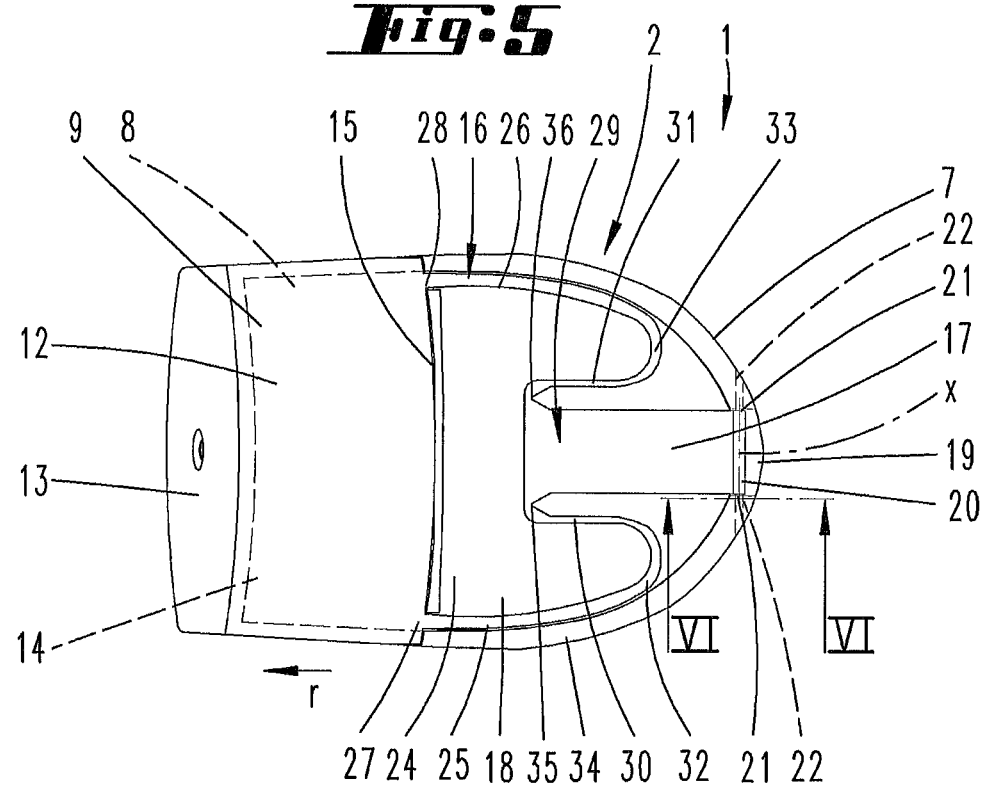
FIG. 5 is a view of the device from below with the mouthpiece in a sealed position according to FIG. 1.
Figure 6:
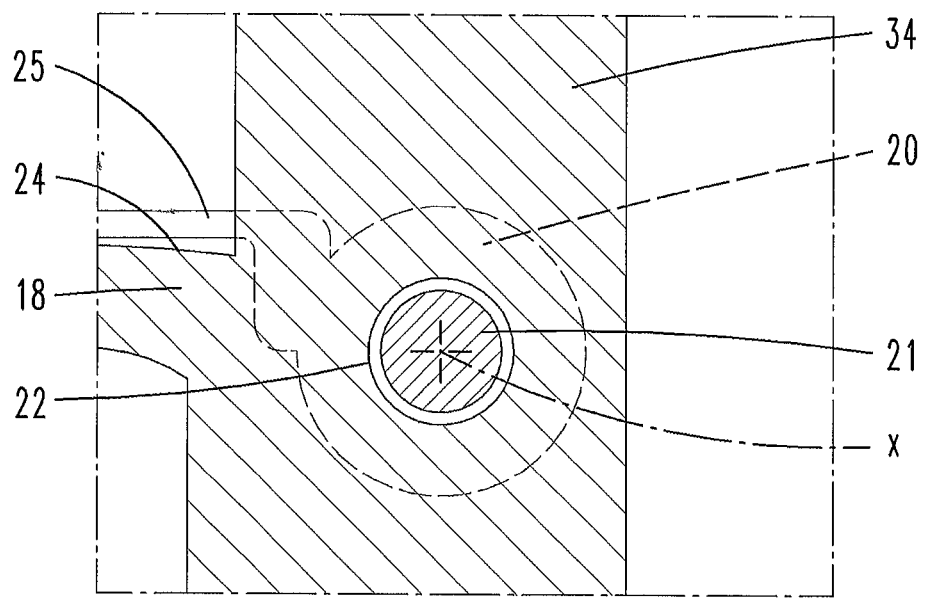
FIG. 6 is the magnified section according to the VI-VI line on FIG. 5.

With reference to a top view according to FIG. 5, in which the swivel axis x is depicted as a line, the spring 16 has a W-shaped design overall. In the W-central region 29 that arises here, the attachment to the attachment region 17 is provided.

This yields a respective spring arm section 30, 31 that runs with a directional component opposite the opening direction 4 for each spring arm 25, 26, at least in the released state of the springs 16, but beyond that also in the sealed position of the mouthpiece according to FIG. 5.

With respect to a horizontal projection according to FIG. 5, each spring arm 25, 26 proceeds from the cap 9, and extends over the free end area of the attachment region 17 in the direction toward the end section 20, here transitions into a reversal section 32, 33 running in a circular ring, which is adjoined by the spring arm section 30, 31 attached to the attachment region 17.

The spring arm sections 30 and 31 are each articulated to the attachment region 17 by a film hinge 35, 36. A thin point (material tapering) with a preferred material thickness of 0.05 to 0.5 mm, in particular of 0.1 to 0.4 mm, arises in the area of the film hinges 35, 36.

Figure 2:
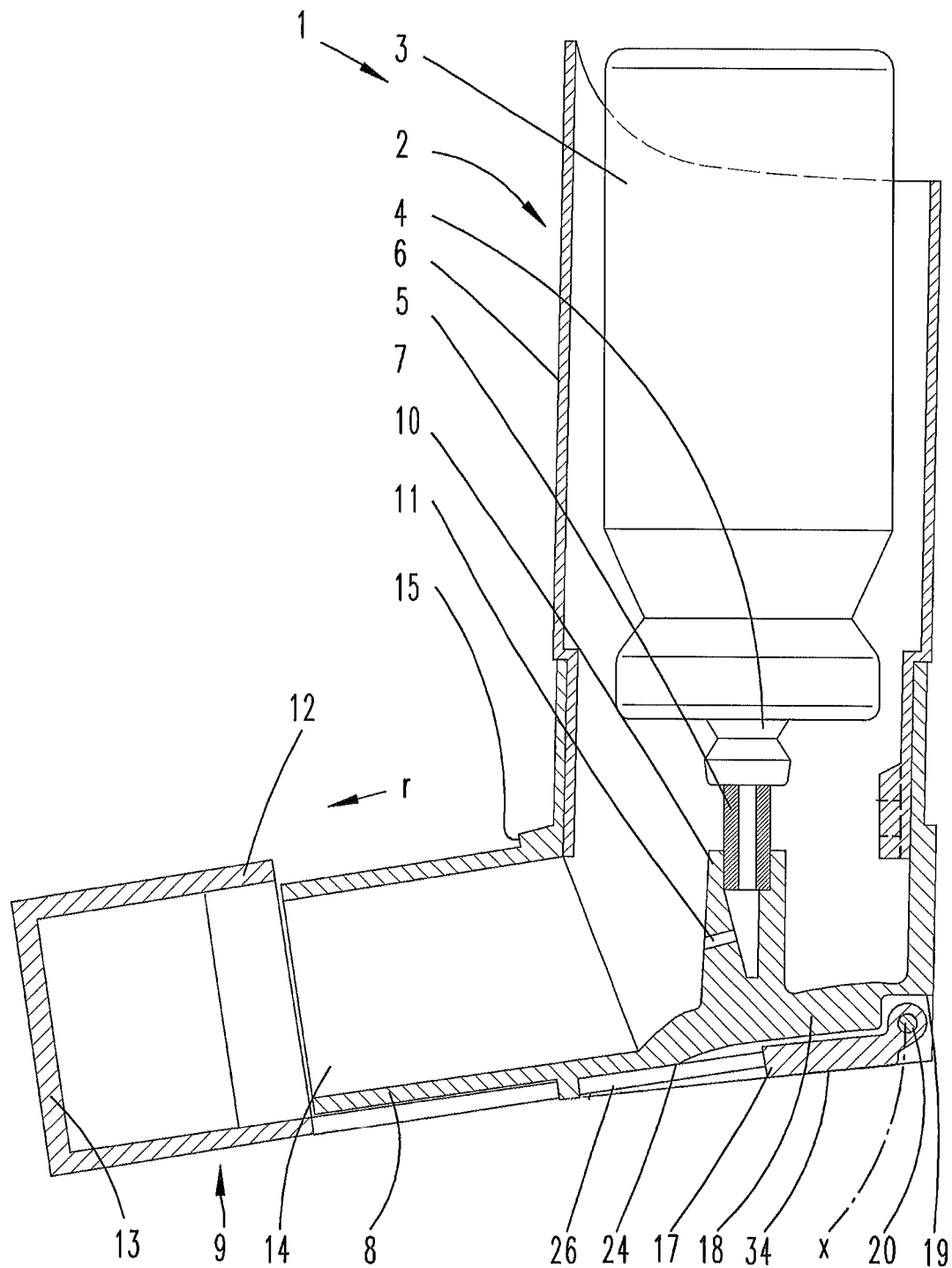
FIG. 2 is an illustration corresponding to FIG. 1 relating to an intermediate position while removing the cap from the mouthpiece.

The reversal section 32, 33 with the adjoining spring arm section 30, 31 provides a spring arm reservoir, so as to lengthen the spring arms 25, 26 while moving the cap 9 to remove it from the mouthpiece 8 (see FIG. 2).

The spring arms 25 and 26 are web-like in design, with a preferred rectangular cross section. It is further preferred that an at least approximately square cross section be provided in the area of the outer W-leg, for example with a respective edge length of 1.3 to 2 mm, further for example 1.6 mm.

By contrast, an elongated, rectangular cross section is preferably provided in the reversal regions 32 and 33, with a height viewed perpendicular to the extension surface of the spring 16 that corresponds to roughly 3 to 4 times the material thickness viewed transverse thereto in the reversal region 32, 33. For example, a height of 2 to 3 mm, preferably of about 2.5 mm, is provided, along with a material thickness of 0.5 to 1 mm, for example of 0.7 mm.

In particular the cross sectional design in the reversal region 32, 33 permits a favorable deflection and spring arm displacement given a shifting of the cap 9 opposite the spring force.

As a whole, the spring 16, in particular each spring arm 25, 26, has an angled progression in the top view according to FIG. 5, further in particular relative to the outer W-sections of the spring 16 to the inner W-legs in the form of the spring arm sections 30, 31.

Both spring arms 25 and 26, along with the springs 16 as a whole, extend in a shared surface, which in the sealed condition of the mouthpiece according to FIG. 1 runs adjusted to the allocation surface 24 of the housing 2, possibly supported thereon.

The spring 16 and attachment region 17 are further preferably encompassed by a housing wall section 34 that extends over the allocation surface 24 of the floor 18, so that the springs 16 and the attachment region 17 extend in a housing floor side depression, in particular in the sealed position of the mouthpiece.

In order to uncover the mouthpiece 8, the cap 9 must be shifted in the opening direction r opposite the prestress of the spring 16, which preferably also acts on the cap 9 in the sealed position of the mouthpiece. Essentially involved here is a linear shifting of the cap 9 relative to the mouthpiece 8.

The spring 16 is hereby further tensioned, accompanied by the quasi-unwinding deflection and lengthening of the spring arms 25, 26.

Figure 3:
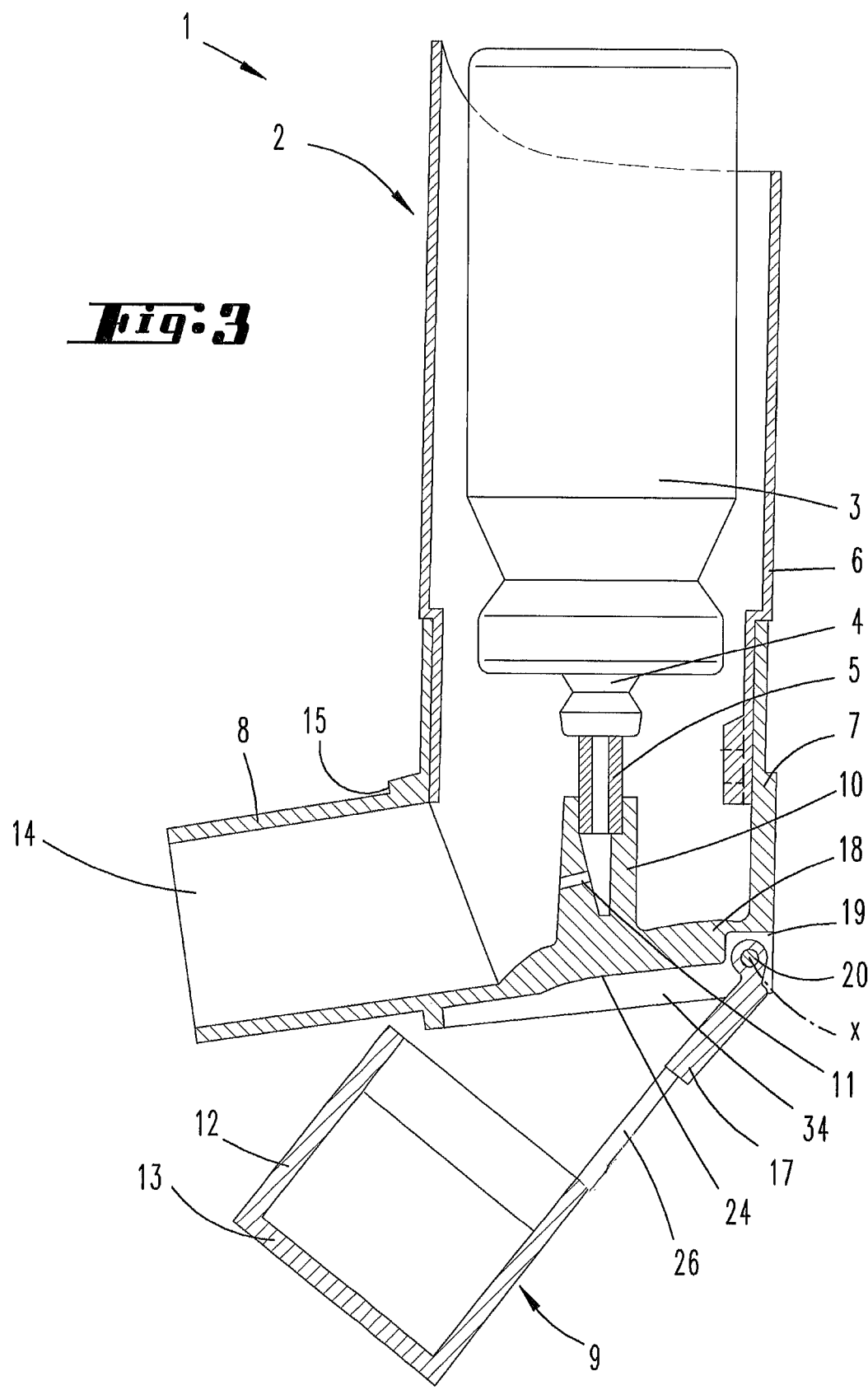
FIG. 3 is a follow-up illustration to FIG. 2 with the mouthpiece released.
Figure 4:
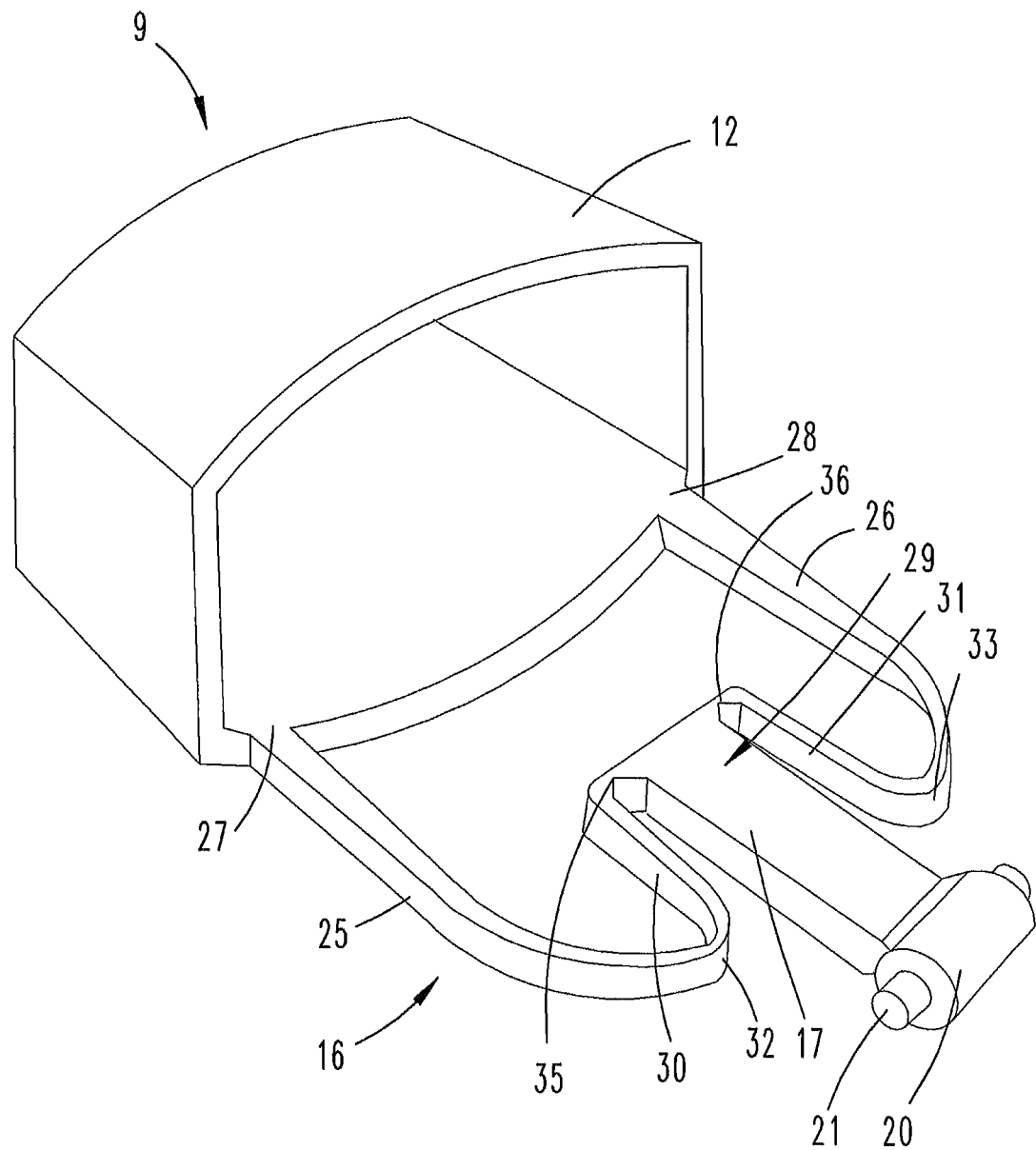
FIG. 4 is a perspective, individual illustration of the cap with a molded on spring.

The cap 9 together with the springs 16 and attachment region 17 can hereafter be downwardly swiveled under the housing floor 18 (see FIG. 3). Discontinuing the tensile stress on the cap 9 yields a released position of the spring 16.

The swivel axis x is transversely directed to the central axis of the body of the ring part 6 enveloping the cartridge 3, as well as transversely directed to a longitudinal central axis of the mouthpiece 8.

If the spring 16 also acts on the cap 9 in the sealed position of the mouthpiece according to FIG. 1, the cap 9 need not be latched to the mouthpiece 8.

The above statements serve to explain the inventions encompassed by the application as a whole, which further develop prior art at least through the following feature combinations, or even independently, specifically:

A handset, characterized in that the spring 16 has an angled progression in a top view, in which the swivel axis x is imaged as a line.

A handset, characterized in that the spring 16 has two spring arms 25, 26, which are joined with the cap 9 at two fastening points 27, 28 spaced apart transversely to the opening direction r.

A handset, characterized in that the cap 9 is to be moved in an opening direction r out of a sealed position into an open position.

A handset, characterized in that, in a released state, the spring 16 as viewed over its length runs partially counter to the opening direction r with one directional component.

A handset, characterized in that the spring arms 25, 26 are brought together on the housing side in a shared attachment region 17.

A handset, characterized in that the attachment region 17 is swivelably connected with the housing 2 by a hinge.

A handset, characterized in that the spring arms 25, 26 extend in a surface which, in the sealed state, runs adjusted to an allocation surface 24 of the housing 2.

A handset, characterized in that the cap 9 abuts against the housing 2 exposed to a prestress in the sealed position.

A handset, characterized in that the spring 16 has a W-shaped design as viewed from above, wherein a W-central region 29 is provided by the attachment region 17.

All disclosed features (taken separately, but also in combination with each other) are essential to the invention. The disclosure of the application hereby also includes the disclosure content of the accompanying/attached priority documents (copy of preliminary application) in its entirety, further with the purpose of also incorporating features in these documents into claims of the present application. The features in the subclaims characterize independent inventive further developments of prior art, in particular so as to initiate partial applications based upon these claims.

| | Reference List |
|---|---|
| 1 | Handset |
| 2 | Housing |
| 3 | Cartridge |
| 4 | Cartridge head |
| 5 | Valve pipe |
| 6 | Ring part |
| 7 | Ring part |
| 8 | Mouthpiece |
| 9 | Cap |
| 10 | Support section |
| 11 | Flow channel |
| 12 | Wall |
| 13 | Cap cover |
| 14 | Mouthpiece opening |
| 15 | Stage |
| 16 | Spring |
| 17 | Attachment region |
| 18 | Housing floor |
| 19 | Depression |
| 20 | End section |
| 21 | Axis |
| 22 | Borehole |
| 23 | — |

-continued

| | Reference List |
|---|---|
| 24 | Allocation surface |
| 25 | Spring arm |
| 26 | Spring arm |
| 27 | Fastening point |
| 28 | Fastening point |
| 29 | W-central region |
| 30 | Spring arm section |
| 31 | Spring arm section |
| 32 | Reversal region |
| 33 | Reversal region |
| 34 | Housing wall section |
| 35 | Film hinge |
| 36 | Film hinge |
| r | Opening direction |
| x | Swivel axis |

The invention claimed is:

1. A handset for delivering and inhaling a pharmaceutical substance, comprising:
    a housing that has a mouthpiece,
    a cap attached to the housing configured for sealing the mouthpiece and being removable from the mouthpiece in a linear opening direction, and
    a spring that attaches the cap to the housing, the spring comprising two spring arms which are joined with the cap at two fastening points that are separated from each other transverse to the opening direction, wherein ends of the spring arms opposite the fastening points merge together on a housing side in a shared attachment region so as to form one piece with the attachment region,
    wherein the spring is angled when viewed in a top view and is elastically deformable along lengths of the spring arms against a tension of the spring wherein the spring is secured under a housing floor, wherein the shared attachment region is directly and swivelably connected with the housing by a hinge, and wherein the cap together with the shared attachment region are configured to be moved in the opening direction against the tension of the spring, which deforms the spring arms to lengthen the spring, and then downwardly swiveled under the housing floor around a swivel axis (x) to release the mouthpiece from the cap.

2. The handset according to claim 1, wherein in a sealed state of the cap, the spring arms extend along an allocation surface of the housing.

3. The handset according to claim 1, wherein in the sealed position, the cap is held against the housing due to the tension of the spring.

4. The handset according to claim 1, wherein the spring has a W-shaped design as viewed from above, and wherein the shared attachment region forms a central region of the W-shaped design.

* * * * *